United States Patent [19]

Schurter et al.

[11] Patent Number: 4,832,736

[45] Date of Patent: May 23, 1989

[54] 3-FLUOROPYRIDYL-2-OXY-PHENOXY DERIVATIVES HAVING HERBICIDAL ACTIVITY

[75] Inventors: Rolf Schurter, Binningen; Konrad Oertle, Therwil, both of Switzerland

[73] Assignee: Ciba-Geigy Corporation, Ardsley, N.Y.

[21] Appl. No.: 130,487

[22] Filed: Dec. 9, 1987

Related U.S. Application Data

[63] Continuation-in-part of Ser. No. 844,407, Mar. 26, 1986, Pat. No. 4,740,235.

[30] Foreign Application Priority Data

Apr. 1, 1985 [CH] Switzerland ............... 1401/85

[51] Int. Cl.$^4$ .................. A01N 43/40; C07F 7/10
[52] U.S. Cl. ........................... 71/94; 546/14; 546/302
[58] Field of Search ................ 546/14; 71/94

[56] References Cited

U.S. PATENT DOCUMENTS 4,518,416  5/1985  Forster et al. .................. 71/94

Primary Examiner—Alan L. Rotman

Attorney, Agent, or Firm—Kevin T. Mansfield; Edward McC. Roberts

[57] ABSTRACT

New 3-fluoropyridyl-2-oxy-phenoxy derivatives are disclosed which have a herbicidal and plant growth inhibiting action. They correspond to the formula

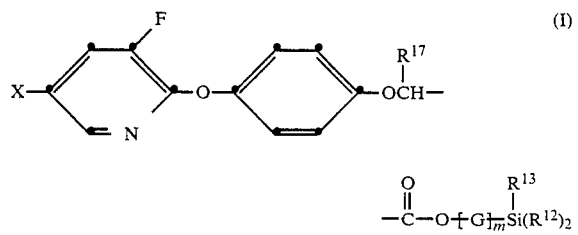

wherein
 X is halogen or trifluoromethyl,
 G is a $C_1$–$C_3$-alkylene chain which can be mono- or disubstituted by methyl or phenyl,
 m is zero or one,
 $R^{12}$ and $K^{13}$ are each $C_1$–$C_6$-alkyl and
 $R^{17}$ is hydrogen, $C_1$–$C_2$-alkyl or methoxymethyl.

These compounds are suitable for the selective control of weeds in crops of cultivated plants, or for the reduction of the growth of grasses.

15 Claims, No Drawings

3-FLUOROPYRIDYL-2-OXY-PHENOXY DERIVATIVES HAVING HERBICIDAL ACTIVITY

In the published European Patent Application EP-A-83 556, there have already been described 3-fluoropyridyl-2-oxy-phenoxy derivatives having herbicidal activity, which correspond to the formula

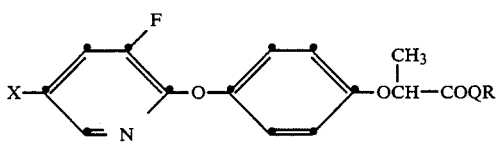

wherein Q is oxygen or sulfur, R is, inter alia, hydrogen, a metal or ammonium ion, or an unsubstituted or substituted $C_1$–$C_9$-alkyl, $C_3$–$C_9$-cycloalkyl, $C_3$–$C_9$-alkynyl or $C_3$–$C_9$-alkynyl group, or a $C_3$–$C_9$-cycloalkenyl group or an imino group, and X is chlorine, bromine or iodine.

The compounds exhibited a good selective-herbicidal action in particular against gramineous weeds in crops of cultivated plants, such as cereals, maize, rice, cotton, soya bean and sugar beet.

It has been shown that a further group of novel 3-fluoropyridyl-2-oxy-phenoxy derivatives have an excellent selective-herbicidal action, both in the pre-emergence and post-emergence process, against in particular gramineous weeds in crops of cultivated plants.

The novel 3-fluoropyridyl-2-oxy-phenoxy derivatives correspond to the formula I

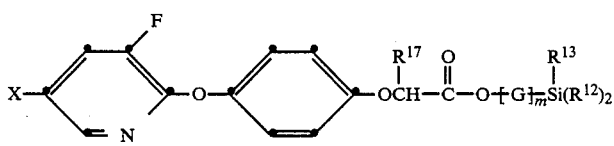

wherein
X is a halogen atom or the trifluoromethyl group,
G is a $C_1$–$C_3$-alkylene chain, which can be mono- or disubstituted by methyl or phenyl,
m is zero or one,
$R^{12}$ and $R^{13}$ are each $C_1$–$C_6$-alkyl and
$R^{17}$ is hydrogen, $C_1$–$C_2$-alkyl or methoxymethyl.

In the above definitions the alkyl moiety can be straight chain or branched. Preferred alkyl rests are methyl, ethyl, n-propyl, isopropyl, n-butyl, isobutyl, sec.butyl, tert.butyl and 2,3-dimethylbutyl etc.

Halogen encompasses fluorine, chlorine, bromine and iodine, preferred is chlorine.

The above definition of G embraces methylene, 1,2-ethylene and 1,3-propylene, and the groups derived therefrom by substitution of 1 or 2 hydrogen atoms by methyl or phenyl, for example: ethylidene, isopropylidene (2,2-propylidene), benzylidene, 1-phenylethylidene, diphenylmethylene, 1,2-propylene, 2,3-butylene, 1,1-dimethyl-1,2-ethylene, 1,1-diphenyl-1,2-ethylene, 1,2-diphenyl-1,2-ethylene, 1-methyl-1-phenyl-1,2-ethylene, 1,2-butylene, 1,3-butylene, 2,2-dimethyl-1,3-propylene, 1-methyl-1-phenyl-1,3-propylene, 1,2-diphenyl-1,3-propylene and 1,3-diphenyl-1,3-propylene.

When m is 1 and G is substituted by methyl or phenyl, or the substituent $R^{17}$ is not hydrogen, then there are asymmetrically substituted carbon atoms present in the molecule. The invention relates to all stereoisomers.

The 3-fluoropyridyl-2-oxy-phenoxy derivatives according to the invention are characterised by a good action against mono- and some dicotyledonous weeds; they are above all effective in the pre- and post-emergence process against undesirable weeds and wild grasses occurring in cultivated crops, such as crops of cereals, maize, rice, soya bean and sugar beet. A particularly valuable aspect is that it is possible with the novel derivatives to combat wild grasses which are otherwise very difficult to control, for example *Avena fatua, Avena sterilis, Alopecurus myosuroides, Lolium perenne*, Phalaris sp., *Bromus tectorum* and various species of Setaria and Panicum. The action under field conditions is achieved even with small applied amounts of less than 1 kg per hectare, at which levels the cultivated crops are not harmed, or are harmed to only a negligible extent.

Halopyridyloxy-α-phenoxy-propionic acid derivatives have been described in numerous publications (cp. for example the German Offenlegungsschriften Nos. 2,546,251, 2,649,706, 2,714,622 and 2,715,284, and the European Publications Nos. 483 and 1473). In these publications, the 3-fluoropyridyl-2-oxy-phenoxy derivatives according to the present invention have in part been taken into account and concomitantly included in the scope. Compounds of this type have never however been produced or tested. They are distinguished from the known halopyridyloxy-α-phenoxy-propionic acids by a stronger action, and hence by the fact that it is possible to use them effectively in smaller amounts. Where the applied amount is sufficiently great however, there also occurs a total-herbicidal action. The novel compounds according to the invention can be applied both in the pre-emergence process and in the post-emergence process. The amounts applied can vary within wide limits, for example between 0.05 and 2 kg of active substance per hectare.

Furthermore, the compounds of the formula I have favourable growth-regulating effects (growth inhibition). They inhibit in particular the growth of grasses.

3-Fluoropyridyl-2-oxy-phenoxy derivatives of the formula I which have proved very active are those which correspond to the formula I wherein X is chlorine or trifluoromethyl, m is one, G is 1–3 alkylene and $R^{12}$, $R^{13}$ and $R^{17}$ are each methyl.

Especially active were the compounds
2-[4-(5-chloro-3-fluoropyridyl-2-oxy)-phenoxy]-propionic acid-trimethylsilyl-methyl ester,
2-[4-(5-chloro-3-fluoropyridyl-2-oxy)-phenoxy]-propionic acid-2'-trimethylsilyl-eth-1'-yl ester,
(2R)-2-[4-(5-chloro-3-fluoropyridyl-2-oxy)-phenoxy]-propionic acid-trimethylsilyl-methyl ester,
(2R)-2-[4-(5-chloro-3-fluoropyridyl-2-oxy)-phenoxy]-propionic acid-2'-trimethylsilyl-eth-1'-yl ester,
(2R)-2-[4-(3-fluoro-5-trifluoromethyl-pyridyl-2-oxy)-phenoxy]-propionic acid-2'-trimethylsilyl-ethyl ester,
(2R)-2-[4-(3-fluoro-5-trifluoromethyl-pyridyl-2-oxy)-phenoxyl]-propionic acid-trimethylsilyl-methyl ester,
2-[4-(3-fluoro-5-trifluoromethyl-pyridyl-2-oxy)-phenoxy]-propionic acid-2'-trimethylsilyl-ethyl ester, 2-[4-(3-fluoro-5-trifluoromethyl-pyridyl-2-oxy)-phenoxy]-propionic acid-trimethylsilyl-methyl ester and
(2R)-2-[4-(5-chloro-3-fluoropyridyl-2-oxy)-phenoxy]-propionic acid dimethyl-(2,3-dimethylbut-2-yl)silyl ester.

The compounds of the formula I are produced by methods known per se.

If m is one, a process comprises reacting a 2,3-difluoropyridine of the formula II

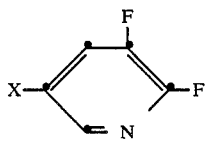
(II)

wherein X has the meaning defined under the formula I, in an inert solvent or diluent and in the presence of the equimolar amount of a base, with a 4-hydroxyphenoxy-α-alkanoic acid derivative of the formula III

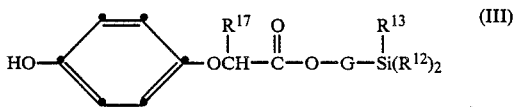
(III)

wherein G, $R^{12}$, $R^{13}$ and $R^{17}$ have the meaning defined under the formula I.

Another process comprises reacting a 4-(3-fluoropyridyl-2-oxy)-phenol of the formula IV

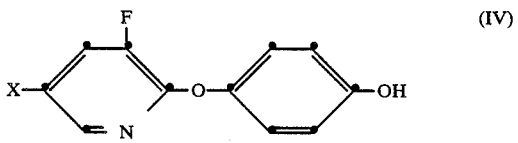
(IV)

wherein X has the meaning defined under the formula I, in an inert solvent or diluent and in the presence of the equimolar amount of a base, with a halide of the formula V

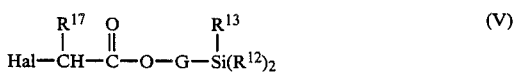
(V)

wherein Hal is chlorine or bromine and G, $R^{12}$, $R^{13}$ and $R^{17}$ have the meaning defined under formula I.

A further process comprises converting a 3-aminopyridyl-2-oxyphenoxy derivative of the formula VI

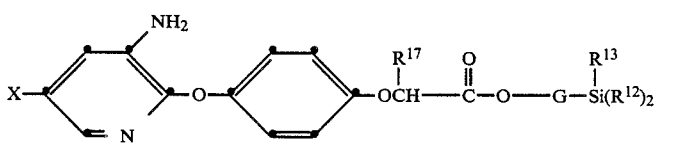
(VI)

wherein X, G, $R^{12}$, $R^{13}$ and $R^{17}$ have the meanings defined under the formula I, using known methods, into a diazonium salt, and converting this further into the fluorine compound.

Another process for producing the compounds of the formula I comprises reacting an acid halide of the formula VII

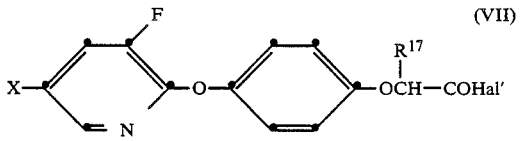
(VII)

wherein Hal' is fluorine, chlorine or bromine, and X and $R^{17}$ have the meanings defined in the foregoing, in an inert solvent or diluent and in the presence of an equimolar amount of a base, with an alcohol or thiol of the formula VIII

(VIII)

wherein G, $R^{12}$ and $R^{13}$ have the meaning defined under the formula I.

A process for producing the compounds of the formula I wherein m is O comprises reacting an acid of the formula IX

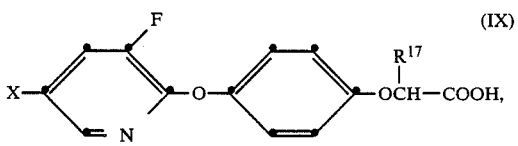
(IX)

wherein X and $R^{17}$ have the meaning defined under the formula I, in an inert solvent, with a silylamide of the formula X

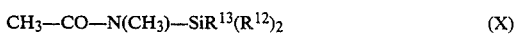
(X)

wherein $R^{12}$ and $R^{13}$ are $C_1$-$C_6$-alkyl.

These reactions are advantageously performed in an organic solvent or diluent to the reactants, for example in an ester, ether or ketone, or in dimethylformamide, dimethyl sulfoxide or acetonitrile, or in an aromatic compound, such as benzene, toluene, and so forth.

The reaction temperatures are between −10° and +150° C., in practice however between room temperature and the boiling point of the solvent. Depending on the chosen starting material, the solvent and the temperature, the reaction time is between one hour up to one day.

Where a halogen atom is detached in the reaction, the equimolar amount of an acid-binding agent should be used. Suitable as such is essentially any inorganic or organic base, for example: NaOH, KOH, NaHCO$_3$, K$_2$CO$_3$ or K-tert-butylate, and amines, such as trimethylamine, triethylamine, pyridine, 4-dimethylaminopyridine, and so forth.

The novel active substances of the formula I are stable compounds which are soluble in customary organic solvents, such as esters, ethers, ketones, and the like.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditisons.

The formulations, that is to say, the compositions or preparations containing the active substance of the formula I and optionally a solid or liquid additive, are produced in a known manner, for example by the intimate mixing and/or grinding of the active substances with extenders, such as with solvents, solid carriers and optionally surface-active compounds (tensides).

Suitable solvents are: aromatic hydrocarbons, preferably the fractions $C_8$ to $C_{12}$, suchas xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil.

The solid carriers used, for example for dusts and dispersible powders, are as a rule natural mineral fillers, such as calcite, talcum, kaolin, montmorillonite or attapulgite. In order to improve the physical properties, it is possible to add highly dispersed silicic acid or highly dispersed absorbent polmers. Suitable granulated adsorptive carriers are porous types, for example pumice, ground brick, sepiolite or bentonite; and suitable non-sorbent carriers are materials such as calcite or sand. There can also be used a great number of pre-granulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are for example the alkali metal, alkaline-earth metal or optionally substituted ammonium salts of high fatty acids ($C_{10}$–$C_{20}$), for example the Na or K salts of oleic or stearic acid, or of natural fatty acid mixtures, which can be obtained for example from coconut oil or tallow oil. Also to be mentioned are the faty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenyl-(4–14)-ethylene oxide adduct.

Suitable nonionic tensides are in particular polyglcol ether derivatives of aliphatic or cycloaliphatic alcohols, saturated or unsaturated fatty acids nd alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylene-diaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenol-polyethoxyethanols, castor oil polyglycol ethers, polypropylene/polyethyleneoxy adducts, tributylphenoxy-polyethoxyethanol, polyethylene glycol and octylphenoxy-polyethoxyethanol. Suitable also are fatty acid esters of polyoxyethylenesorbitan, such as polyoxyethylenesorbitan-triolate.

In the case of the cationic tensides, they are in particular quaternary ammonium salts which contain as N-substituents at least one alkyl group having 8 to 22 carbon atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:

"Mc Cutcheon's Detergents and Emulsifiers Annual", MC Publishing Corp., Ridgewood, New Jersey,m 1979;

H. Stache, "Tensid Taschenbuch", 2nd Edition, C. Hanser Verlag, Munich and Vienna, 1981; and M. and J. Ash, "Encyclopedia of Surfactants", Vol. I–III, Chemical Publishing Co., New York, 1980–81.

These preparations contain as a rule 0.1 to 99%, particularly 0.1 to 95%, of active substance of the formula I, 1 to 99% of a solid or liquid additive, and 0 to 25%, especially 0.1 to 25%, of a tenside.

Whereas commercial products are preferably in the form of concentrated compositions, the preparations employed by the end-user are as a rule diluted.

The compositions can also contain further additives, such as stabilisers, antifoaming agents, viscosity regulators, binders and adhesives, and also fertilisers or other active ingredients for obtaining special effects.

The following Examples describe in detail the production of the 3-fluoropyridyl-2-oxy-phenoxy derivatives of the formula I according to the invention, and of compositions containing such compounds as active ingredients. Further esters according to the invention which are obtained in an analogous manner are listed in the Tables following the Examples. Temperatures are given in degrees Centigrade and percentage values relate to weight.

EXAMPLE 1

Production of
(R)-2-[4-(3-fluoro-5-trifluoromethyl-pyridin-2-yloxy)-phenoxy]-propionic acid-2'-trimethylsilyl-ethyl ester

A solution of 2.3 ml (0.016 mol) of trimethylsilylethanol and 1.2 ml (0.016 mol) of pyridine in 90 ml of ethylacetate are cooled to 10° while stirring. Then a solution of 5.20 g (0.14 mol) of (R)-2-[4-(3-fluoro-5-trifluoromethyl-pyridin-2-yloxy)-phenoxy]-propionic acid chloride in 20 ml of ethylacetate is added thereto dropwise during one hour. The reaction mixture is then stirred for 16 hours during which time the temperature rises to room temperature. It is then washed with water and a concentrated salt solution, dried over magnesium sulfate filtered and concentrated. The residue is purified by passing through a short chromatography column (eluant petrol ether/ether 2:1). The title product is thus obtained in a yield of 5.2 g (84%) as an oil with refraction index $n_D^{30}$ 1.4891.

The (R)-2-[4-(3-fluoro-5-trifluoromethylpyridin-2-yloxy)-phenoxy]-propionic acid chloride necessary as starting material is obtained as follows:

(a)

4-(3-fluoro-5-trifluoromethylpyridin-2-yloxy)-phenol

A mixture of 16.5 g (0.15 mol) of hydroquinone, 19.1 g (0.3 mol) of potassium hydroxide (88%) in 600 ml of dimethylsulfoxide is stirred at room temperature under a nitrogen atmosphere until everything is dissolved. A solution of 13.7 g (0.075 mol) of 2,3-difluoro-5-trifluoromethyl-pyridine in 25 ml of dimethylsulfoxide is added dropwise at a temperature of 15°–20°. The reaction mixture is then stirred at room temperature for 24 hours. Then it is poured into ice/water and the mixture is acidified with hydrochloric acid, extracted with methylene chloride, washed with water, dried over magnesium sulfate, filtered and evaporated to dryness. The residue crystallizes in hexane/ethyl acetate to yield 14.5 g (71%) of white crystals, melting at 97°.

(b)

(R)(+)-2-[4-(3-fluoro-5-trifluoromethylpyridin-2-yloxy)-phenoxy]-propionic acid methyl ester A solution of 12.5 g (0.046 mol) of 4-(3-fluoro-5-trifluoropyridin-2-yloxy)-phenol in 40 ml of dimethylsulfoxide is added dropwise to a stirred solution of 6.35 g (0.046 mol) of potassium carbonate in 50 ml of dimethylsulfoxide. When everything is added, the mixture is stirred for 2 hours at room temperature and then a solution of 11.9 g (0.046 mol) of (S)(−)-lactic acid-methylester tosylate in 20 ml of dimethylsulfoxide is added dropwise over 30 minutes. The mixture is heated to 60° and stirred at that temperature for 20 hours, then poured onto ice/water and the organic material is extracted three times with ether. The ether-layer is washed with water and saturated salt solution, dried over magnesium sulfate, filtered and evaporated. The residue is passed for purification through a silicagel column with a hexane/ethyl acetate 3:1 solvent. After distillation of the solvent, 12.4 g (75%) of a clear oil of the above ester is obtained ($[α]_D^{20} = +33.8±0.5°$ 2% in acetone).

(c)

(R)(+)-2-[4-(3-fluoro-5-trifluoromethylpyridin-2-yloxy)-phenoxy]-propionic acid

To a solution of 9.4 g (0.026 mol) of (R)(+)-2-[4-(3-fluoro-5-trifluoromethylpyridin-2-yloxy)-phenoxy]-propionic acid-methyl ester in 65 ml of dioxane are added 28.5 ml of 1N sodium hydroxide and the mixture is stirred for five hours at a temperature of 35°. Then it is poured onto an ice/water mixture and acidified with hydrochloric acid. The organic material is extracted therefrom twice with ethyl acetate. The organic layers are washed with water and dried over magnesium sulfate, filtered and concentrated. The residue is cristallized in ethyl acetate/hexane and yields 8.0 g (89%) of the above (R)(+)-[4-(3-fluoro-5-trifluoromethylpyridin-2-yloxy-phenoxy]-propionic acid as white crystals.

(d)

(R)-2-[4-(3-fluoro-5-trifluoromethylpyridin-2-yloxy)-phenoxy]-propionic acid chloride 5.15 g (0.015 mol) of (R)-2-[4-(3-fluoro-5-trifluoromethylpyridin-2-yloxy)-phenoxy]-propionic acid are dissolved in 45 ml of toluene. Then 10 ml of toluene are distilled off in an oil-bath that has a temperature of 130°. The reaction mixture is then cooled down to 90° and 3.6 g of thionyl chloride are added slowly thereto. The mixture is stirred for 16 hours at 90° and then evaporated under reduced pressure. The title compound is obtained as an oil.

EXAMPLE 2

Preparation of
(R)-2-[4-(5-chloro-3-fluoropyridin-2-yloxy)-phenoxy]-propionic acid-2,3-dimethylbut-2-yl-dimethyl-silyl ester

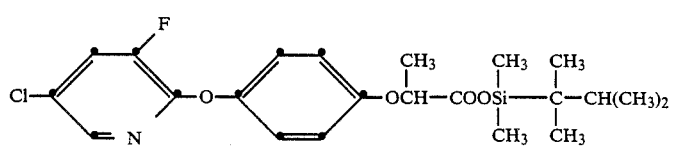

A solution of 3.0 g (9.36 mmol) of (R)-2-[4-(5-chloro-3-fluoropyridin-2-yl-oxy)-phenoxy]-propionic acid, 2.48 g (11.55 mmol) of N-(Dimethyl-[2,3-dimethylbut-2-yl]- silyl)-N-methyl-acetamide in 20 ml of acetonitrile is stirred at room temperature for 18 hours. The solution is then concentrated under reduced pressure and the residue is taken up in 20 ml of hexane and 20 ml of cyclohexane. This solution is washed three times with dimethylformamide and then concentrated under reduced pressure. The residue is the above ester.

Yield 4.06 g (74%) of a colorless oil.

The (R)-2-[4-(5-chloro-3-fluoropyridin-2-yloxy)-phenoxy)]-propionic acid necessary as starting material is obtained as follows:

(a)

4-(5-chloro-3-fluoropyridin-2-yloxy)-phenol

A mixture of 27.5 g (0.25 mol) of hydroquinone, 11.2 g (0.2 mol) of potassium hydroxide in 600 ml of dimethylsulfoxide is stirred at room temperature under a nitrogen atmosphere until everything is dissolved. A solution of 30 g (0.2 mol) of 5-chloro-2,3-difluoropyridine in 200 ml of dimethylsulfoxide is added dropwise thereto. The reaction mixture is then heated to 70° and stirred at that temperature for 4 hours. Then it is poured into ice/water and the mixture is acidified with hydrochloric acid, extracted with ethyl acetate, dried over magnesium sulfate, filtered and evaporated to dryness. The residue is taken up in a hexane/ethyl acetate 2:1 solvent and passed over a silocagel column for purification. After concentrating the eluate, the residue crystallizes to yield 33 g of white crystals, melting at 97°–98°.

(b)

(R)(+)-2-[4-(5-chloro-3-fluoropyridin-2-yloxy)-phenoxy]-propionic acid methyl ester A solution of 24 g (0.1 mol) of 4-(5-chloro-3-fluoropyridin-2-yloxy)-phenol in 80 ml of dimethylsulfoxide is added dropwise to a stirred solution of 13.8 g (0.1 mol) of potassium carbonate in 50 ml of dimethylsulfoxide. When everything is added, the mixture is stirred for 2 hours at room temperature and then 25.8 g (0.1 mol) of (S)(−)-lactic acid-methylester tosylate is added dropwise over 30 minutes. The mixture is heated to 60° and stirred at that temperature for 20 hours, then poured onto ice/water and the organic material is extracted three times with ether. The ether-layer is washed with water and saturated salt solution, dried over magnesium sulfate, filtered and evaporated. The residue is passed for purification through a silicagel column with a hexane/ethyl acetate 3:1 solvent. After distillation of the solvent, 26 g of a clear oil of the above ester is obtained ($[\alpha]_D^{20} = +38.8 \pm 0.5°$ 2% in acetone).

(c)

(R)(+)-2-[4-(5-chloro-3-fluoropyridin-2-yloxy)-phenoxy]-propionic acid

To a solution of 13.0 g (0.04 mol) of (R)(+)-2-[4-(5-chloro-3-fluoropyridin-2-yloxy]-methyl ester in 65 ml of dioxane are added 42 ml of 1N sodium hydroxide and the mixture is stirred for 2½ hours at a temperature of 35°. Then it is poured onto an ice/water mixture and acidified with 22 ml of 2N hydrochloric acid. The organic material is extracted therefrom twice with ethyl acetate. The organic layers are washed with a saturated salt solution and dried over magnesium sulfate, filtered and concentrated. The residue is cristallized in ethyl acetate/hexane and yields 10.2 g (81.8%) of the above (R)(+)-[4-(5-chloro-3-fluoropyridin-2-yloxy)-phenoxy]-propionic acid as white crystals, which melt at 95°–96° ($[\alpha]_D^{20} = +37.5 \pm 0.5°$ 2% in acetone).

The following compounds are produced in a manner analogous to that of the above Examples.

TABLE 1

$$X-\underset{N}{\underset{\|}{\text{pyridine-F}}}-O-\text{phenyl}-OCH(CH_3)-COO-[G]_m-Si(R^{12})_2R^{13}$$

| No. | X | [G]$_m$ | R$^{12}$ | R$^{13}$ | Observations | Physical properties |
|---|---|---|---|---|---|---|
| 1.01 | Cl | —CH$_2$—CH$_2$— | CH$_3$ | CH$_3$ | 2R—enantiomer | n$_D^{35}$ 1.5181 <br> $[\alpha]_D^{20}$ = +37.0° (acetone) |
| 1.02 | Cl | —CH$_2$— | CH$_3$ | CH$_3$ | 2R—enantiomer | n$_D^{35}$ 1.5201 <br> $[\alpha]_D^{20}$ = +41.3° (acetone) |
| 1.03 | CF$_3$ | —CH$_2$— | CH$_3$ | CH$_3$ | racemate | m.p. 61–63° C. |
| 1.04 | CF$_3$ | —CH$_2$—CH$_2$— | CH$_3$ | CH$_3$ | racemate | n$_D^{35}$ 1.4842 |
| 1.05 | Cl | —CH$_2$—CH$_2$— | CH$_3$ | CH$_3$ | racemate | n$_D^{35}$ 1.5201 |
| 1.06 | Cl | —CH$_2$— | CH$_3$ | CH$_3$ | racemate | n$_D^{35}$ 1.5155 |
| 1.07 | Cl | —CH$_2$— | C$_2$H$_5$ | C$_2$H$_5$ | | |
| 1.08 | Cl | —CH$_2$—CH$_2$— | C$_2$H$_5$ | C$_2$H$_5$ | | |
| 1.09 | Cl | —CH(CH$_3$)—CH$_2$— | CH$_3$ | CH$_3$ | | |
| 1.10 | Cl | —CH$_2$CH(CH$_3$)— | CH$_3$ | CH$_3$ | | |
| 1.11 | Cl | —CH(CH$_3$)— | CH$_3$ | CH$_3$ | | |
| 1.12 | CF$_3$ | —CH(CH$_3$)— | CH$_3$ | CH$_3$ | | |
| 1.13 | CF$_3$ | —CH$_2$—CH$_2$— | CH$_3$ | CH$_3$ | 2R—enantiomer | n$_D^{30}$ 1.4891 |
| 1.14 | Cl | — | CH$_3$ | C(CH$_3$)$_2$CH(CH$_3$)$_2$ | racemate | |
| 1.15 | Cl | — | CH$_3$ | C(CH$_3$)$_2$CH(CH$_3$)$_2$ | R—enantiomer | oil |
| 1.16 | CF$_3$ | — | CH$_3$ | C(CH$_3$)$_2$CH(CH$_3$)$_2$ | racemate | |
| 1.17 | CF$_3$ | — | CH$_3$ | C(CH$_3$)$_2$CH(CH$_3$)$_2$ | R—enantiomer | |

EXAMPLE 3

Production of a formulation with liquid active ingredients of the formula I (% =percent by weight)

| Emulsion concentrates | a | b | c |
|---|---|---|---|
| 2-[4-(5-chloro-3-fluoropyridyl-2-oxy)-phenoxy]-propionic acid | 20% | 40% | 50% |

-continued

| Emulsion concentrates | a | b | c |
|---|---|---|---|
| trimethylsilyl-methyl ester | | | |
| calcium dodecylbenzenesulfonate | 5% | 8% | 5.8% |
| castor oil-polyethylene glycol ether (35 mols of ethylene oxide) | 5% | — | — |
| tributylphenol-polyethylene glycol (30 mols of ethylene oxide) | — | 12% | 4.2% |
| cyclohexanone | — | 15% | 20% |
| xylene mixture | 70% | 25% | 20% |

Emulsions of any required concentration can be produced from concentrates of this type by dilution with water.

| Solutions | a | b | c | d |
|---|---|---|---|---|
| active ingredient according Table 1 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| Granulates | a | b |
|---|---|---|
| active ingredient according to Table 1 | 5% | 10% |
| kaolin | 94% | — |
| highly dispersed silicic acid | 1% | — |
| attapulgite | — | 90% |

The active ingredient is dissolved in methylene chloride; the solution is subsequently sprayed onto the carrier, and the solvent is evaporated off in vacuo.

| Dusts | a | b |
|---|---|---|
| active ingredient from Table 1 | 2% | 5% |
| highly dispersed silicic acid | 1% | 5% |
| talcum | 97% | — |
| kaolin | — | 90% |

Dusts ready for use are obtained by the intimate mixing together of the carriers with the active ingredient.

Formulation Examples for solid active ingredients of the formula I (% = percent by weight)

| Wettable powders | a | b |
|---|---|---|
| active ingredient from Table 1 | 20% | 60% |
| sodium lignin sulfonate | 5% | 5% |
| sodium lauryl sulfate | 3% | — |
| sodium diisobutylnaphthalene sulfonate | — | 6% |
| octylphenolpolyethylene glycol ether (7–8 mols of ethylene oxide) | — | 2% |
| highly dispersed silicic acid | 5% | 27% |
| kaolin | 67% | — |

The active ingredient is well mixed with the additives and the mixture is thoroughly ground in a suitable mill. Wettable powders which canbe diluted with water to give suspensions of the required concentration are obtained.

| Emulsion concentrate | |
|---|---|
| active ingredient from Table 1 | 10% |
| octylphenol polyethylene glycol ether (4–5 mols of ethylene oxide) | 3% |
| calcium dodecylbenzenesulfonate | 3% |
| castor oil polyglykol ether (36 mols of ethylene oxide) | 4% |
| cyclohexanone | 30% |
| xylene mixture | 50% |

Emulsions of the concentration required can be obtained from this concentrate by dilution with water.

| Dusts | a | b |
|---|---|---|
| active ingredient from Table 1 | 5% | 8% |
| talcum | 95% | — |
| kaolin | — | 92% |

Dusts ready for use are obtained by mixing the active ingredient with the carriers and grinding the mixture in a suitable mill.

| Extruder granulate | |
|---|---|
| active ingredient from Table 1 | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and then dried in a stream of air.

| Coated granulate | |
|---|---|
| active ingredient from Table 1 | 3% |
| polyethylene glycol (M.W. 200) | 3% |
| kaolin | 94% |

The finely ground active ingredient is evenly applied, in a mixer, to the kaolin moistened with polyethylene glycol. Dustfree coated granulates are obtained in this manner.

| Suspension concentrate | |
|---|---|
| active ingredient from Table 1 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which canbe produced, by dilution with water, suspensions of the concentration required.

EXAMPLE 6

Testing of the herbicidal action

Pre-emergence herbicidal action (inhibition of germination)

Immediately after sowing of the test plants in pots in a greenhouse, the surface of the soil is sprayed with an aqueous dispersion of the active ingredient, which has been prepared either from a 25% emulsion concentrate, or from a 25% wettable powder in the case of active ingredients which cannot be prepared as emulsion concentrates owing to inadequate solubility. Various concentrations are used, and the amount of active ingredient is calculated on the basis of kg per hectare. The pots are then kept in a greenhouse at 22°–25° C. with 50–70% relative humidity, and are regularly watered. The test results are evaluated after three weeks.

The tested compounds from Table 1 exhibit a good to very good phytotoxic action against the monocotyledons used in the tests.

Post-emergence herbicidal action (contact herbicide)

A number of weeds and cultivated plants, are grown in pots in a greenhouse, and after emergence (in the 4- to 6-leaf stage) the plants are sprayed with an aqueous active-ingredient dispersion in dosages of 125 and 60 grams of active ingredient per hectare, and the treated plants are kept at 24°–26° C. with 45–60% relative humidity. The test is evaluated two weeks after the treatment and the state of the plants is assessed according to the following scale 9 plant grows normally, like untreated control plants
6–8 slight damage which the plant can outgrow after the effect of the substance wears off
5 plant stunted
2–4 severe phytotoxic damage, plant crippled
1 plant dead.

The results are given in Table 2 below.

TABLE 2

| compound tested | 1.04 | | 1.13 | |
|---|---|---|---|---|
| application rate | 125 g/ha | 60 g/ha | 125 g/ha | 60 g/ha |
| plant | | | | |
| Avena fatua | 1 | 2 | 1 | 2 |
| Bromus tectorum | 1 | 3 | 2 | 3 |
| Lolium perenne | 1 | 2 | 1 | 1 |
| Sorghum halepense | 1 | 1 | 1 | 1 |
| soya | 9 | 9 | 9 | 9 |
| cotton | 9 | 9 | 9 | 9 |
| sun-flower | 9 | 9 | 9 | 9 |
| sugar-beet | 9 | 9 | 9 | 9 |

Reduction of growth of grasses

Seeds of the grasses *Lolium perenne, Poa pratensis, Festuca ovina* and *Dactylis glomerata* are sown in a soil/peat/sand mixture (6:3:1) in plastic trays and watered in the usual manner. The emerged grasses are cut back each week to a height of 4 cm, and are sprayed 40 days after sowing and 1 day after the last cutting with an aqueous spray liquor of in each case a compound of the formula I. The amount of active ingredient is equivalent to 0.05–2 kg of active ingredient per hectare. The growth of the grasses is compared, 10 and 21 days after application, with that of the untreated control specimens. The tested compounds from Table 1 in an applied amount of 0.05 kg per hectare reduce the growth of the grasses by 13–32%.

We claim:

1. A 3-fluoropyridyl-2-oxy-phenoxy derivative of the formula I $$X-\text{(pyridyl-F)}-O-\text{(phenyl)}-OCH(R^{17})-COO-(G)_m-Si(R^{12})_2 R^{13} \quad (I)$$

wherein
X is halogen or trifluoromethyl,
G is a $C_1$–$C_3$-alkylene chain which can be mono- or disubstituted by methyl or phenyl,
m is zero or one,
$R^{12}$ and $R^{13}$ are each $C_1$–$C_6$-alkyl and
$R^{17}$ is hydrogen, $C_1$–$C_2$-alkyl or methoxymethyl.

2. A 3-fluoropyridyl-2-oxy-phenoxy derivative of the formula I according to claim 1, wherein X is chlorine or trifluoromethyl, G is $C_1$–$C_3$-alkylene, and $R^{12}$, and $R^{13}$ and $R^{17}$ are each methyl.

3. 2-[4-(5-Chloro-3-fluoropyridyl -2-oxy)-phenoxy]-propionic acidtrimethylsilyl-methyl ester according to claim 1.

4. 2-[4-(5-Chloro-3-fluoropyridyl-2-oxy)-phenoxy]-propionic acid-2'trimethylsilyl-eth-1'-yl ester according to claim 1.

5. (2R)-2-[4-(5-Chloro-3-fluoropyridyl-2-oxy)-phenoxy]-propionic acid-trimethylsilyl-methyl ester according to claim 1.

6. (2R)-2-[4-(5-Chloro-3-fluoropyridyl-2-oxy)-phenoxy]-propionic acid-2'-trimethylsilyl-ethyl ester according to claim 1.

7. (2R)-2-[4-(3-Fluoro-5-trifluoromethyl-pyridyl-2-oxy)-phenoxy]-proionic acid-2'-trimethylsilyl-ethyl ester according to claim 1.

8. (2R)-2-[4-(3-Fluoro-5-trifluoromethyl-pyridyl-2-oxy)-phenoxy]-propionic acid-trimethylsilyl-methyl ester according to claim 1.

9. 2-[4-(3-Fluoro-5-trifluoromethyl -pyridyl-2-oxy)-phenoxy]-propionic acid-2'-trimethylsilyl-ethyl ester according to claim 1.

10. 2-[4-(3-Fluoro-5-trifluoromethyl -pyridyl-2-oxy)-phenoxy]-propionic acid-trimethylsilyl-methyl ester according to claim 1.

11. (2R)-2-[4-(5-Chloro-3-fluoropyridin-2-yloxy)-phenoxy]-propionic acid dimethyl-(2,3-dimethylbut-2-yl)-silyl ester according to claim 1.

12. A herbicidal and plant-growth-inhibition composition comprising, as active ingredient, a herbicidally and plant-growth inhibiting amount of a 3-fluoropyridyl-2-oxy-phenoxy derivative of the formula I according to claim 1 together with inert carrier material.

13. A method of selectively controlling gramineous weeds, which method comprises applying thereto or to the locus thereof a herbicidally effective amount of a 3-fluoropyridyl-2-oxy-phenoxy derivative of the formula I according to claim 1.

14. A compound of the formula I according to claim 1 wherein X is trifluoromethyl.

15. A method of inhibiting growth of grasses, which method comprises applying thereto or to the locus thereof an effective amount of a 3-fluoropyridyl-2-oxy-phenoxy derivative of the formula I according to claim 1.

* * * * *